United States Patent
Ueno

(10) Patent No.: US 8,268,297 B2
(45) Date of Patent: Sep. 18, 2012

(54) HAIR COSMETIC COMPOSITION

(75) Inventor: Masako Ueno, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/744,933

(22) PCT Filed: Nov. 26, 2008

(86) PCT No.: PCT/JP2008/003476
§ 371 (c)(1),
(2), (4) Date: May 27, 2010

(87) PCT Pub. No.: WO2009/069288
PCT Pub. Date: Jun. 4, 2009

(65) Prior Publication Data
US 2010/0322885 A1    Dec. 23, 2010

(30) Foreign Application Priority Data
Nov. 27, 2007 (JP) ................ 2007-306397

(51) Int. Cl.
A61K 8/34 (2006.01)
A61K 8/362 (2006.01)
A61K 8/365 (2006.01)
A61K 8/92 (2006.01)
A61Q 5/00 (2006.01)

(52) U.S. Cl. ............ 424/70.1; 424/70.31; 132/202
(58) Field of Classification Search .......... None
See application file for complete search history.

(56) References Cited

U.S. PATENT DOCUMENTS

| 6,923,954 B2 * | 8/2005 | Doi et al. ............ 424/70.19 |
| 2005/0196369 A1 | 9/2005 | Ueyama et al. |
| 2006/0165624 A1 * | 7/2006 | Ueyama et al. ........ 424/70.11 |
| 2009/0068134 A1 | 3/2009 | Kaharu |

FOREIGN PATENT DOCUMENTS

| CN | 1679476 A | 10/2005 |
| JP | 2004 189727 | 7/2004 |
| JP | 2005 239565 | 9/2005 |
| JP | 2005 239568 | 9/2005 |
| JP | 2005 239569 | 9/2005 |
| JP | 2005 239663 | 9/2005 |
| JP | 2005 239667 | 9/2005 |
| JP | 2006 290796 | 10/2006 |
| JP | 2006 347996 | 12/2006 |
| JP | 2007 186473 | 7/2007 |
| JP | 2007 186474 | 7/2007 |
| JP | 2007 217372 | 8/2007 |
| JP | 2007 223931 | 9/2007 |

* cited by examiner

Primary Examiner — Ernst Arnold
Assistant Examiner — Christopher R Lea
(74) Attorney, Agent, or Firm — Oblon, Spivak, McClelland, Maier & Neustadt, L.L.P.

(57) ABSTRACT

A hair cosmetic composition, containing the following Components (A) to (D):
(A) benzyl alcohol, from 0.1 to 2% by mass;
(B) dipropylene glycol, from 0.5 to 20% by mass;
(C) malic acid or a salt thereof, from 0.2 to 10% by mass, in terms of the malic acid; and
(D) lactic acid or a salt thereof, from 0.2 to 10% by mass, in terms of the lactic acid; and optionally containing a surfactant (E) at a concentration of 2% by mass or less and at a Component (E)/Component (A) mass ratio falling within a range of from 0 to 5.

11 Claims, No Drawings

HAIR COSMETIC COMPOSITION

FIELD OF THE INVENTION

The present invention relates to hair cosmetic compositions.

BACKGROUND OF THE INVENTION

In recent years, it has been said that owing to the influence of chemical treatment caused by, for example, hair coloring or physical treatment caused by blowing, cuticles on the hair surface peel off or the hair becomes porous by the efflux of lipids from the inside of the hair and as a result, the hair becomes excessively dry, resistant to finger combing, unmanageable and lusterless.

Leave-on hair cosmetic compositions mainly used now include emulsion type products such as hair cream containing wax, higher alcohol and surfactant to provide the hair with manageability and protect the hair from excessive dryness; and gel type products containing a film forming polymer (set polymer). Such hair cosmetic compositions can temporarily solve the problems such as poor manageability and excessive dryness by causing an oil or fat or polymer to adhere to the hair surface, but cannot fundamentally improve the hair luster or manageability.

Some hair cosmetic compositions for improving the hair quality are known and compositions using a specific organic acid and organic solvent, on which an attempt was made to improve the hair quality by acting on the inside of the hair, are known. Of these, leave-on hair cosmetic compositions containing both malic acid and lactic acid as the organic acid and further containing an organic solvent are proposed (refer to Patent Document 1). Continuous use of this hair cosmetic composition can gradually improve the hair luster and especially improve the set retention property under high humidity, manageability, and hair feel. Such a hair cosmetic composition is disclosed also in Patent Documents 2 and 3.

The hair cosmetic composition disclosed in Patent Document 1 has good affinity to either wet hair or dry hair when the composition is applied thereto, but it does not enable sufficient smooth finger combing. In addition, even after continuous use, it does not have a sufficient effect of improving manageability, particularly under high humidity. The hair cosmetic composition disclosed in Patent Document 2 or 3, on the other hand, does not have a satisfactory effect on affinity and finger combability when applied to dry hair or wet hair (especially, dry hair). In addition, continuous use thereof does not have a satisfactory effect of improving manageability/finger combability or improving manageability under high humidity.

[Patent Document 1] JP-A-2004-189727
[Patent Document 2] JP-A-2007-186474 (Example 10)
[Patent Document 3] JP-A-2006-290796 (Example 6 and Example 8)

SUMMARY OF THE INVENTION

The present invention provides a hair cosmetic composition, which contains the following Components (A) to (D):
 (A) benzyl alcohol, from 0.1 to 2% by mass;
 (B) dipropylene glycol, from 0.5 to 20% by mass;
 (C) malic acid or a salt thereof, from 0.2 to 10% by mass, in terms of the malic acid; and
 (D) lactic acid or a salt thereof, from 0.2 to 10% by mass, in terms of the lactic acid; and optionally contain a surfactant (E) at a concentration of 2% by mass or less and at the same, at a Component (E)/Component (A) mass ratio falling within a range of from 0 to 5.

The present invention also provides a hair-quality improving method including applying the hair cosmetic composition to the hair and leaving the resulting hair without rinsing.

DETAILED DESCRIPTION OF THE INVENTION

The present invention relates to a hair cosmetic composition capable of providing the hair with good affinity, smooth finger combability, and good hair feel; bringing about an effect of improving the manageability of the hair either before rinsing or after rinsing when it is continuously applied about three times; and preventing the unmanageability of the hair under high humidity.

The present inventors have found that a hair cosmetic composition capable of satisfying the above-described requirement can be obtained by using two specific organic solvents and two specific organic carboxylic acids in combination and limiting the content of a surfactant to a predetermined level or less.

The content of benzyl alcohol as Component (A) should be from 0.1 to 2% by mass, preferably from 0.12 to 1.5% by mass, more preferably from 0.15 to 1.2% by mass from the standpoint of its ability of improving affinity to the hair, improving softness of the hair at the time of application and further, improving the manageability of the hair.

The content of dipropylene glycol as Component (B) in the hair cosmetic composition of the present invention should be from 0.5 to 20% by mass, preferably from 1 to 15% by mass, more preferably from 1.5 to 10% by mass from the standpoint of its ability of contributing to the solubilization or stable dispersion of Component (A) and synergistically acting with Component (A) to promote an effect of improving luster or manageability of the hair.

A Component (B)/Component (A) mass ratio is preferably from 1 to 50, more preferably from 3 to 45, even more preferably from 5 to 40 from the standpoint that Component (A) and Component (B) synergistically act to promote an improvement in the luster or manageability of the hair, and impart the hair with good affinity and softness.

The content of malic acid or a salt thereof, as Component (C) in the hair cosmetic composition of the present invention should be from 0.2 to 10% by mass, preferably from 0.25 to 8% by mass, even more preferably from 0.3 to 6% by mass in terms of malic acid, from the standpoint of satisfying both smooth finger combability to wet hair and smooth finger combability to dry hair and imparting a manageability improving effect.

The content of lactic acid or a salt thereof, as Component (D) in the hair cosmetic composition of the present invention should be from 0.2 to 10% by mass, preferably from 0.25 to 8% by mass, more preferably from 0.3 to 6% by mass in terms of lactic acid, from the standpoint of imparting the hair with flexibility, luster and good affinity.

The total content of Component (C) and Component (D) in the hair cosmetic composition of the present invention is preferably from 0.4 to 15% by mass, more preferably from 0.5 to 14% by mass, even more preferably from 0.6 to 12% by mass in terms of an acid converted from the total amount of the acids and salts thereof, from the standpoint of imparting good finger combability and smoothness to the hair without causing stickiness or stiffness.

A surfactant as Component (E) may be added to the hair cosmetic composition of the present invention at a concentration of 2% by mass or less and at the same time at a Component (E)/Component (A) mass ratio falling within a range of from 0 to 5. The content of the surfactant, if it is added, is preferably from 0.02 to 2% by mass, more preferably from 0.05 to 1.5% by mass from the standpoint of promoting penetration of Component (A) into the hair and promoting an effect of improving manageability. From the same standpoint, the Component (E)/Component (A) mass ratio is preferably from 0 to 5, more preferably from 0.5 to 4.5, even more preferably from 1 to 4. As the surfactant, any of cationic surfactants, nonionic surfactants, amphoteric surfactants, and anionic surfactants is usable, of which cationic surfactants are preferred.

For example, the following cationic surfactants (i) to (vi) are suited for use. Of these, the cationic surfactants (i), (iii), and (v) are preferred.

(i) Alkyltrimethylammonium Salts

Examples include those represented by the following formula:

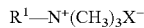

$R^1-N^+(CH_3)_3 X^-$

[wherein $R^1$ represents an alkyl group having from 12 to 22 carbon atoms, and $X^-$ represents a halide ion (preferably, chloride ion or bromide ion)].

Specific examples include cetyltrimethylammonium chloride, stearyltrimethylammonium chloride and behenyltrimethylammonium chloride.

(ii) Alkoxyalkyltrimethylammonium Salts

Examples include those represented by the following formula:

$R^1-O-R^2-N^+(CH_3)_3 X^-$

[wherein, $R^2$ represents an ethylene or trimethylene group, and $R^1$ and $X^-$ have the same meanings as described above].

(iii) Dialkyldimethylammonium Salts

Examples include those represented by the following formula:

$R^3{}_2 N^+(CH_3)_2 X^-$

[wherein, $R^3$ represents an alkyl group having from 12 to 22 carbon atoms or a benzyl group and $X^-$ has the same meaning as described above].

Specific examples include dialkyldimethylammonium chloride.

(iv) Alkyldimethylamines and Salts Thereof

Examples include those represented by the following formula:

$R^1-N(CH_3)_2$

[wherein, $R^1$ has the same meaning as described above].

(v) Alkoxyalkyldimethylamines and Salts Thereof

Examples include those represented by the following formula:

$R^1-O-R^2-N(CH_3)_2$

[wherein, $R^1$ and $R^2$ have the same meanings as described above].

Specific examples include N,N-dimethyl-3-octadecyloxypropylamine and N,N-dimethyl-3-hexadecyloxypropylamine.

(vi) Alkylamidoalkyldimethylamines and Salts Thereof

Examples include those represented by the following formula:

$R^4-C(=O)NH-R^2-N(CH_3)_2$

[wherein, $R^4$ represents an alkyl group having from 11 to 21 carbon atoms and $R^2$ has the same meaning as described above].

Examples of the anionic surfactant include alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, α-sulfofatty acid salts, N-acylamino acid surfactants, mono- or di-phosphate surfactants and sulfosuccinate salts.

Examples of the counterion to the anionic residue of the above-described anionic surfactants include alkali metal ions such as sodium ion and potassium ion, alkaline earth metal ions such as calcium ion and magnesium ion, ammonium ions, and alkanolamines having from 1 to 3 alkanol groups with 2 or 3 carbon atoms (such as monoethanolamine, diethanolamine, triethanolamine and triisopropanolamine).

Examples of the nonionic surfactant include polyoxyalkylene alkyl ethers, polyoxyalkylene alkenyl ethers, higher fatty acid sucrose esters, polyglycerin fatty acid esters, higher fatty acid mono- or diethanolamides, polyoxyethylene hydrogenated castor oils, polyoxyethylene sorbitan fatty acid esters, polyoxyethylene sorbitol fatty acid esters, alkyl saccharide surfactants, alkylamine oxides, and alkyl amidoamine oxides. Of these, polyoxyalkylene alkyl ethers and polyoxyethylene hydrogenated castor oils are preferred, with polyoxyethylene alkyl ethers being more preferred.

As the amphoteric surfactant, imidazolines, carbobetaines, amidobetaines, sulfobetaines, hydroxysulfobetaines, and amidosulfobetaines may be used.

In the hair cosmetic composition of the present invention, 2-benzyloxyethanol may be incorporated as Component (F) at a concentration of 0.5% by mass or less and at the same time, at a Component (F)/Component (A) mass ratio falling within a range of from 0 to 0.5. The content of 2-benzyloxyethanol is preferably 0.5% by mass or less, more preferably 0.2% by mass or less from the standpoint of promoting manageability while imparting softness, luster feel and smooth finger combability to the hair.

In the hair cosmetic composition of the present invention, a conditioning component selected from silicones and oily substances may be incorporated in order to improve a conditioning effect further. Examples of the silicones include dimethylpolysiloxanes, polyether-modified silicones, amino-modified silicones, carboxy-modified silicones, methylphenylpolysiloxane, fatty acid-modified silicones, alcohol-modified silicones, aliphatic alcohol-modified silicones, epoxy-modified silicones, fluorine-modified silicones, cyclic silicones, and alkyl-modified silicones. Of these, dimethylpolysiloxanes, polyether-modified silicones and amino-modified silicones are preferred. Dimethylpolysiloxanes can provide the hair with good lubricity, polyether-modified silicones can provide the hair with smoothness, and amino-modified silicones can provide the hair with moist feel. In the present invention, various silicones may be used either singly or in combination of two or more, depending on the desired performance. As the dimethylpolysiloxane, those having a viscosity of from about 5 mm²/s to about 10 million mm²/s may be used depending on the desired feel of the hair, wherein those having a viscosity of about 10 million mm²/s are often supplied in the form of an emulsion. Of these, those having a viscosity of from 5000 mm²/s to 10 million mm²/s are preferred, with those having a viscosity of from 50000 mm²/s to 10 million mm²/s being more preferred. The term "polyether-modified silicones" is a generic name of polyoxyethylene/methylpolysiloxane copolymers and poly(oxyethylene/oxypropylene)methylpolysiloxane copolymers and those having various HLBs are known. Examples of the commercially available products thereof include "Silicone KF351A", "Silicone KF353A", "Silicone KF6008", "Silicone KF6016", "Silicone KF6011", and "Silicone KF6012", each, product of Shin-etsu Chemical, and "SH3771C", "SH3773C", and "SH3775C", each, product of Dow Corning Toray. As the amino-modified silicones, amodimethicone oil or an emulsion thereof is preferred. Their commercially available products are, for example, amodimethicone emulsion "SM8704C", product of Dow Corning Toray, and "KT-1989", "XF-42-B1989", product of Momentive Performance Materials Japan.

The content of the silicones in the hair cosmetic composition of the present invention is preferably from 0.05 to 20% by mass, more preferably from 0.1 to 10% by mass, even more preferably from 0.3 to 5% by mass in consideration of smooth finger combability and stickiness-free feel.

The oily substances are preferably used to improve the hair manageability after drying. Examples thereof include hydrocarbons such as squalene, squalane, liquid isoparaffin, light liquid isoparaffin, heavy liquid isoparaffin, α-olefin oligomer, liquid paraffin, and cycloparaffin; glycerides such as castor oil, cacao oil, mink oil, avocado oil, and olive oil; waxes such as sperm wax, lanolin, microcrystalline wax, ceresin wax, and carnauba wax; higher alcohols such as cetyl alcohol, oleyl alcohol, stearyl alcohol, isostearyl alcohol, 2-octyldodecanol, myristyl alcohol, behenyl alcohol, and cetostearyl alcohol; esters such as octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut oil fatty acid, isostearic acid, isopalmitic acid, and lanolin fatty acid; and other oily substances such as isostearyl glyceryl ether and polyoxypropylene butyl ether. Of these, branched hydrocarbons including squalene, squalane, liquid isoparaffin, light liquid isoparaffin, heavy liquid isoparaffin, and α-olefin oligomer are preferred.

The content of the oily substance in the hair cosmetic composition of the present invention is preferably from 0.05 to 20% by mass, more preferably from 0.1 to 10% by mass, even more preferably from 0.5 to 5% by mass from the standpoint of good manageability and stickiness-free feel.

The hair cosmetic composition of the present invention may further contain, according to the purpose of use, another component ordinarily employed for hair cosmetic compositions. Examples include organic solvents other than Components (A) and (B) such as phenoxyethanol, propylene glycol, N-methylpyrrolidone, propylene carbonate; polymer compounds such as cationic cellulose, hydroxyalkylated celluloses and highly polymerized polyethylene oxide; anti-dandruffs such as zinc pyrithione and benzalkonium chloride; vitamin preparations; bactericides; anti-inflammatory agents; preservatives; chelating agents; humectants such as panthenol; colorants such as dyes and pigments; extracts such as extract of Eucalyptus in a polar solvent, protein available from a shell having a pearl layer or a pearl itself or hydrolysate of the protein, protein available from silk or hydrolysate of the protein, protein-containing extract available from seeds of legume plants, Panax ginseng extract, rice bran extract, fucoid extract, camellia extract, aloe extract, Alpinia leaf extract, and chlorella extract; pearl powder such as mica titanium; perfumes; coloring matters; ultraviolet absorbers; antioxidants; pH adjusters such as organic acids other than Components (C) and (D), e.g., citric acid and glycolic acid and alkali agents, e.g., sodium hydroxide and potassium hydroxide; and components listed in ENCYCLOPEDIA OF SHAMPOO INGREDIENTS (MICELLE PRESS).

The hair cosmetic composition of the present invention preferably has a pH (at 25° C.) of from 3.0 to 5.0 when diluted to 20 times the mass with water. The hair cosmetic composition having a pH within the above-described range has a function of repairing a hair damage caused by coloring or the like and is excellent in the function of giving good softness and a supple touch to the hair during the period from wetting to after drying. The pH is adjusted to preferably from 3.2 to 4.7, more preferably from 3.4 to 4.4 from the standpoint of the repairing effect of damaged hair. For pH adjustment, an acid substance such as inorganic acid or organic acid and a basic substance such as sodium hydroxide may be used in combination. Examples of the organic acid include those exemplified above as Components (C) and (D).

The form of the hair cosmetic composition of the present invention may be selected from liquid, gel, paste, cream, and wax as needed. The composition in solution form using, as a solvent, water or a lower alcohol is preferred, with the composition in aqueous solution form being more preferred.

The hair cosmetic composition of the present invention is used preferably as a hair conditioning agent or hair styling agent. It may be provided, for example, as a pump spray, aerosol spray, pump foam, aerosol foam, gel, or lotion.

The hair cosmetic composition of the present invention can provide a hair-quality improving effect when applied to the hair and left on the hair without rinsing it away. The term "left on the hair without rinsing it away" means that the hair cosmetic composition is left on the hair for at least 3 hours, preferably at least 6 hours from its application to the hair to shampooing thereafter.

Treatment of the hair with the hair cosmetic composition of the present invention, at least once in two days and at least two times, preferably three times in total is effective for improving the manageability of the hair itself and finger combability.

EXAMPLES

Examples 1 to 11, Comparative Examples 1 to 20

The hair cosmetic compositions shown in Tables 2 to 4 are prepared in a conventional manner and evaluated using the following method in accordance with the following criteria.

Evaluation methods of "spreadability and affinity upon application to wet hair", "finger combability upon application to wet hair", "spreadability and affinity upon application to dry hair", "finger combability upon application to dry hair", "finger combability of dry hair after successive three times application", and "improvement in manageability of hair after successive three times application".

1) Hair Tress to be Evaluated (Common to Every Evaluation)

A hair tress of 15 cm in length, 3 cm in width and 3 g in weight is prepared by using the hair of a Japanese female not subjected to chemical treatment such as permanent waving and hair coloring. The hair tress is bleached (with "Prettia", soft bubble bleach Hi-bleach; product of Kao Corporation) two times and the resulting hair tress is provided for the evaluation.

2) Treatment of the Hair Tress 2-1) Hair Tresses for Evaluating "Spreadability and Affinity Upon Application to Wet Hair" and "Finger Combability upon Application to Wet Hair"

The hair tresses to be evaluated were shampooed with a plain shampoo ("Curel", a shampoo manufactured by Kao Corporation, which will hereinafter be called "plain shampoo") and towel-dried. Then, 0.3 g of each of the hair cosmetic compositions shown in Tables 2 to 4 was applied uniformly to each of the resulting hair tresses and spreadability and affinity of the composition were evaluated. The finger combability of each hair tress was then evaluated by using the hair tress combed with a ring comb ("New Delrin metaling Comb No. 1", product of Delrin, which will hereinafter be called "ring comb") for 10 seconds.

2-2) Hair Tresses for Evaluating "Spreadability and Affinity Upon Application to Dry Hair" and "Finger Combability Upon Application to Dry Hair"

The hair tresses to be evaluated were shampooed with the plain shampoo and towel-dried. The resulting hair tresses were each dried by combing it with the ring comb for 5 minutes under warm wind of 70° C. Then, 0.3 g of each of the hair cosmetic compositions shown in Tables 2 to 4 was applied to the resulting hair tress uniformly and spreadability and affinity of the composition were evaluated. Then, the hair tress combed with the ring comb for 10 seconds was evaluated for its finger combability.

2-3) Hair Tresses for Evaluating "Finger Combability of Dry Hair after Successive Three Times Application" and "Improvement in Manageability of Hair after Successive Three Times Application"

The hair tresses to be evaluated were shampooed with the plain shampoo and towel-dried. Then, 0.3 g of each of the hair cosmetic compositions shown in Tables 2 to 4 was applied to each of the resulting hair tresses and dried by combing it with the ring comb for 5 minutes under warm wind of 70° C. The warm wind used here has, as well as a function of drying the hair tress, a function of promoting the state under which the composition is left to stand in evaluating the effect produced by leaving the composition without rinsing it away. The treatment from shampooing to drying was performed three times in total.

With regard to the "finger combability of dry hair after successive three times application", finger combability after the treatment (before shampooing) and that after the treatment, shampooing and then drying in a similar manner (after shampooing) were evaluated.

With regard to the "improvement in manageability of hair after successive three times application", the improvement after the treatment (before shampooing) and that after the treatment, shampooing and drying in a similar manner (after shampooing) were evaluated after leaving the hair tress for 15 minutes under normal environment (60% RH, 25° C.) and high-humidity environment (90% RH, 25° C.)

3) Evaluation Criteria

Sensual evaluation was made by a panel of five experts in accordance with the table of evaluation criteria shown in Table 1. Each expert evaluated with from 1 to 5 scores. In Tables 2 to 4, a total evaluation score of five experts is shown.

TABLE 1

|  | 5 | 4 | 3 | 2 | 1 |
|---|---|---|---|---|---|
| Spreadability and affinity upon application to wet hair | Superior | A little superior | Mean | A little Inferior | Inferior |
| Finger combability upon application to wet hair | Superior | A little superior | Mean | A little Inferior | Inferior |
| Spreadability and affinity upon application to dry hair | Superior | A little superior | Mean | A little Inferior | Inferior |
| Finger combability upon application to dry hair | Superior | A little superior | Mean | A little Inferior | Inferior |
| Finger combability of dry hair after successive three times application | Superior | A little superior | Mean | A little Inferior | Inferior |
| Improvement in manageability of hair after successive three times application (comparison with that before treatment) | Superior | A little superior | No improvement | A little Inferior | Inferior |

TABLE 2

| | | (% by mass) | Examples | | | | | |
|---|---|---|---|---|---|---|---|---|
| | | | 1 | 2 | 3 | 4 | 5 | 6 |
| (A) | Benzyl alcohol | | 0.2 | 0.5 | 0.3 | 1 | 0.2 | 2 |
| (B) | Dipropylene glycol | | 2 | 3 | 5 | 5 | 2 | 1 |
| (C) | Malic acid | | 0.6 | 0.3 | 0.3 | 0.3 | 8 | 0.6 |
| (D) | Lactic acid | | 0.6 | 0.3 | 0.3 | 0.3 | 8 | 0.6 |
| (E) | Polyoxyethylene hydrogenated castor oil (40EO) | | 0.6 | 1.5 | 1 | 1.5 | 0.6 | 0.6 |
| (F) | 2-Benzyloxyethanol | | — | — | — | — | — | — |
| | pH Adjuster (sodium hydroxide/citric acid) | | q.s. | q.s. | q.s. | q.s. | q.s. | q.s. |
| | Purified water | | Balance | Balance | Balance | Balance | Balance | Balance |
| (E)/(A) Mass ratio | | | 3 | 3 | 3.3 | 1.5 | 3 | 2 |
| (C) + (D) | | | 1.2 | 0.6 | 0.6 | 0.6 | 16 | 1.2 |
| (B)/(A) Mass ratio | | | 10 | 6 | 16.7 | 5 | 10 | 0.5 |
| pH (When diluted to 20 times with water, 25° C.) | | | 3.7 | 3.7 | 3.7 | 3.7 | 3.7 | 3.7 |
| Evaluation | Before shampooing | Spreadability and affinity upon application to wet hair | 25 | 24 | 22 | 21 | 22 | 19 |
| | | Finger combability upon application to wet hair | 23 | 22 | 22 | 21 | 16 | 18 |
| | | Spreadability and affinity upon application to dry hair | 25 | 24 | 22 | 21 | 22 | 18 |
| | | Finger combability upon application to dry hair | 23 | 22 | 23 | 22 | 18 | 17 |
| | | Finger combability of dry hair after successive three times application | 24 | 23 | 24 | 23 | 19 | 17 |

TABLE 2-continued

|  |  |  | | | | | | |
|---|---|---|---|---|---|---|---|---|
| | | Improvement in manageability of hair after successive three times application | 23 | 25 | 25 | 25 | 24 | 22 |
| | | Manageability of hair under high humidity after successive three times application | 22 | 24 | 25 | 25 | 23 | 21 |
| | After shampooing | Finger combability of dry hair after successive three times application | 22 | 22 | 22 | 21 | 17 | 16 |
| | | Improvement in manageability of hair after successive three times application | 22 | 23 | 23 | 24 | 22 | 21 |
| | | Manageability of hair under high humidity after successive three times application | 21 | 23 | 22 | 23 | 21 | 20 |

| | | | Examples | | | | |
|---|---|---|---|---|---|---|---|
| | | (% by mass) | 7 | 8 | 9 | 10 | 11 |
| (A) | Benzyl alcohol | | 0.18 | 1.5 | 0.4 | 0.4 | 0.2 |
| (B) | Dipropylene glycol | | 10 | 2 | 15 | 17.6 | 2 |
| (C) | Malic acid | | 0.6 | 0.6 | 0.3 | 0.3 | 5 |
| (D) | Lactic acid | | 0.6 | 0.6 | 0.3 | 0.3 | 5 |
| (E) | Polyoxyethylene hydrogenated castor oil (40EO) | | 0.6 | 0.6 | 1 | 1 | 0.6 |
| (F) | 2-Benzyloxyethanol | | — | 0.6 | — | — | — |
| | pH Adjuster (sodium hydroxide/citric acid) | | q.s. | q.s. | q.s. | q.s. | q.s. |
| | Purified water | | Balance | Balance | Balance | Balance | Balance |
| (E)/(A) Mass ratio | | | 3.3 | 0.4 | 2.5 | 2.5 | 3 |
| (C) + (D) | | | 1.2 | 1.2 | 0.6 | 0.6 | 10 |
| (B)/(A) Mass ratio | | | 55.6 | 1.3 | 37.5 | 44 | 10 |
| pH (When diluted to 20 times with water, 25° C.) | | | 3.7 | 3.7 | 3.7 | 3.7 | 3.7 |
| Evaluation | Before shampooing | Spreadability and affinity upon application to wet hair | 21 | 19 | 24 | 19 | 23 |
| | | Finger combability upon application to wet hair | 19 | 17 | 21 | 18 | 21 |
| | | Spreadability and affinity upon application to dry hair | 19 | 18 | 22 | 17 | 23 |
| | | Finger combability upon application to dry hair | 18 | 14 | 22 | 16 | 21 |
| | | Finger combability of dry hair after successive three times application | 19 | 16 | 23 | 20 | 22 |
| | | Improvement in manageability of hair after successive three times application | 21 | 22 | 24 | 25 | 25 |
| | | Manageability of hair under high humidity after successive three times application | 20 | 21 | 21 | 23 | 24 |
| | After shampooing | Finger combability of dry hair after successive three times application | 16 | 16 | 20 | 17 | 22 |
| | | Improvement in manageability of hair after successive three times application | 20 | 23 | 22 | 22 | 23 |
| | | Manageability of hair under high humidity after successive three times application | 19 | 22 | 20 | 20 | 21 |

TABLE 3

| | | | Comparative Examples | | | | | | |
|---|---|---|---|---|---|---|---|---|---|
| | | (% by mass) | 1 | 2 | 3 | 4 | 5 | 6 | 7 |
| (A) | Benzyl alcohol | | — | 0.05 | 5 | 0.2 | 0.2 | 0.2 | 0.5 |
| (B) | Dipropylene glycol | | 2 | 2 | 2 | — | 0.05 | 25 | 2 |
| (C) | Malic acid | | 0.6 | 0.6 | 0.6 | 0.6 | 0.6 | 0.6 | — |
| (D) | Lactic acid | | 0.6 | 0.6 | 0.6 | 0.6 | 0.6 | 0.6 | 0.6 |
| (E) | Polyoxyethylene hydrogenated castor oil (40EO) | | 0.6 | 0.2 | 0.6 | 0.6 | 0.6 | 0.6 | 0.6 |
| | pH Adjuster(Na hydroxide/citric acid) | | q.s. | q.s. | q.s. | q.s. | q.s. | q.s. | q.s. |
| | Purified water | | Balance | Balance | Balance | Balance | Balance | Balance | Balance |
| (E)/(A) Mass ratio | | | — | 4 | 0.12 | 3 | 3 | 3 | 1.2 |
| (C) + (D) | | | 1.2 | 1.2 | 1.2 | 1.2 | 1.2 | 1.2 | 0.6 |
| (B)/(A) Mass ratio | | | — | 40 | 0.4 | — | 0.25 | 125 | 4 |

TABLE 3-continued

| | | | | | | | | | |
|---|---|---|---|---|---|---|---|---|---|
| pH (When diluted to 20 times with water, 25° C.) | | | 3.7 | 3.7 | 3.7 | 3.7 | 3.7 | 3.7 | 3.7 |
| Evaluation | Before shampooing | Spreadability and affinity upon application to wet hair | 14 | 16 | 14 | 14 | 13 | 9 | 14 |
| | | Finger combability upon application to wet hair | 14 | 14 | 9 | 13 | 13 | 8 | 13 |
| | | Spreadability and affinity upon application to dry hair | 14 | 15 | 13 | 13 | 14 | 9 | 16 |
| | | Finger combability upon application to dry hair | 13 | 13 | 7 | 12 | 12 | 7 | 14 |
| | | Finger combability of dry hair after successive three times application | 16 | 16 | 7 | 12 | 13 | 8 | 14 |
| | | Improvement in manageability of hair after successive three times application | 15 | 16 | 14 | 14 | 13 | 11 | 14 |
| | | Manageability of hair under high humidity after successive three times application | 14 | 16 | 12 | 12 | 13 | 11 | 14 |
| | After shampooing | Finger combability of dry hair after successive three times application | 11 | 11 | 13 | 9 | 9 | 12 | 8 |
| | | Improvement in manageability of hair after successive three times application | 13 | 14 | 21 | 13 | 15 | 23 | 10 |
| | | Manageability of hair under high humidity after successive three times application | 12 | 14 | 20 | 13 | 14 | 23 | 10 |

| | | | Comparative Examples | | | | | | |
|---|---|---|---|---|---|---|---|---|---|
| | | (% by mass) | 8 | 9 | 10 | 11 | 12 | 13 | 14 |
| (A) | Benzyl alcohol | | 0.5 | 0.5 | 0.5 | 0.5 | 0.5 | 0.6 | 0.15 |
| (B) | Dipropylene glycol | | 2 | 2 | 2 | 2 | 2 | 2 | 2 |
| (C) | Malic acid | | 0.05 | 15 | 0.6 | 0.6 | 0.6 | 0.6 | 0.6 |
| (D) | Lactic acid | | 0.6 | 0.6 | — | 0.05 | 15 | 0.6 | 0.6 |
| (E) | Polyoxyethylene hydrogenated castor oil (40EO) | | 0.6 | 0.6 | 0.6 | 0.6 | 0.6 | 2.5 | 1 |
| | pH Adjuster(Na hydroxide/citric acid) | | q.s. | q.s. | q.s. | q.s. | q.s. | q.s. | q.s. |
| | Purified water | | Balance | Balance | Balance | Balance | Balance | Balance | Balance |
| (E)/(A) Mass ratio | | | 1.2 | 1.2 | 1.2 | 1.2 | 1.2 | 4.2 | 6.7 |
| (C) + (D) | | | 0.65 | 15.6 | 0.6 | 0.65 | 15.6 | 1.2 | 1.2 |
| (B)/(A) Mass ratio | | | 4 | 4 | 4 | 4 | 4 | 3.3 | 13.3 |
| pH (When diluted to 20 times with water, 25° C.) | | | 3.7 | 3.7 | 3.7 | 3.7 | 3.7 | 3.7 | 3.7 |
| Evaluation | Before shampooing | Spreadability and affinity upon application to wet hair | 14 | 12 | 12 | 15 | 11 | 12 | 13 |
| | | Finger combability upon application to wet hair | 13 | 6 | 11 | 13 | 7 | 9 | 11 |
| | | Spreadability and affinity upon application to dry hair | 14 | 9 | 11 | 14 | 11 | 11 | 14 |
| | | Finger combability upon application to dry hair | 13 | 7 | 7 | 11 | 6 | 9 | 11 |
| | | Finger combability of dry hair after successive three times application | 14 | 7 | 6 | 11 | 7 | 10 | 10 |
| | | Improvement in manageability of hair after successive three times application | 14 | 15 | 17 | 14 | 16 | 19 | 13 |
| | | Manageability of hair under high humidity after successive three times application | 13 | 14 | 15 | 12 | 15 | 20 | 11 |
| | After shampooing | Finger combability of dry hair after successive three times application | 12 | 7 | 9 | 8 | 8 | 14 | 13 |
| | | Improvement in manageability of hair after successive three times application | 11 | 21 | 14 | 18 | 22 | 18 | 12 |
| | | Manageability of hair under high humidity after successive three times application | 11 | 20 | 12 | 19 | 23 | 17 | 11 |

TABLE 4

|  |  | (% by mass) | Comparative Examples | | | | | |
|---|---|---|---|---|---|---|---|---|
|  |  |  | 15 | 16 | 17 | 18 | 19 | 20 |
| (A) |  | Benzyl alcohol | 0.2 | — | 2.5 | 0.2 | — | 0.2 |
| (B) |  | Dipropylene glycol | 3 | — | — | 3 | 2 | — |
| (C) |  | Malic acid | 0.1 | 2.5 | 2.5 | 0.1 | 0.6 | 0.6 |
| (D) |  | Lactic acid | 0.5 | 2.5 | 2.5 | 0.5 | 0.6 | 0.6 |
| (E) |  | Polyoxyethylene hydrogenated castor oil (40EO) | — | 0.25 | 0.25 | — | 0.6 | 0.6 |
|  |  | Stearic acid dimethylaminopropylamide | 2 | — | — | — | — | — |
|  |  | Octylamidopropyl benzalkonium chloride | 0.3 | — | — | — | — | — |
|  |  | Stearyl trimethylammonium chloride | — | 0.25 | 0.25 | — | — | — |
|  |  | Behenic acid dimethylaminopropylamide (*) | — | — | — | 2 | — | — |
|  |  | Behenyltrimethylammonium chloride | — | — | — | 0.3 | — | — |
| (F) |  | 2-Benzyloxyethanol | — | 2.5 | — | — | 0.2 | — |
|  |  | Propylene glycol | — | — | 2.5 | — | — | 2.0 |
|  |  | pH Adjuster (sodium hydroxide/citric acid) | q.s. | q.s. | q.s. | q.s. | q.s. | q.s. |
|  |  | Purified water | Balance | Balance | Balance | Balance | Balance | Balance |
| (E)/(A) Mass ratio |  |  | 11.5 | — | 0.2 | 11.5 | — | 3 |
| (C) + (D) |  |  | 0.6 | 5 | 5 | 0.6 | 1.2 | 1.2 |
| (B)/(A) Mass ratio |  |  | 15 | — | — | 15 | — | — |
| pH (when diluted to 20 times with water, 25° C.) |  |  | 3.2 | 3.7 | 3.7 | 3.7 | 3.7 | 3.7 |
| Evaluation | Before shampooing | Spreadability and affinity upon application to wet hair | 14 | 19 | 14 | 15 | 18 | 18 |
|  |  | Finger combability upon application to wet hair | 13 | 18 | 12 | 14 | 18 | 16 |
|  |  | Spreadability and affinity upon application to dry hair | 9 | 19 | 12 | 11 | 14 | 14 |
|  |  | Finger combability upon application to dry hair | 9 | 12 | 11 | 8 | 13 | 14 |
|  |  | Finger combability of dry hair after successive three times application | 12 | 12 | 12 | 9 | 13 | 14 |
|  |  | Improvement in manageability of hair after successive three times application | 12 | 16 | 13 | 15 | 14 | 14 |
|  |  | Manageability of hair under high humidity after successive three times application | 13 | 15 | 12 | 13 | 13 | 14 |
|  | After shampooing | Finger combability of dry hair after successive three times application | 11 | 14 | 10 | 14 | 18 | 13 |
|  |  | Improvement in manageability of hair after successive three times application | 11 | 11 | 17 | 16 | 16 | 13 |
|  |  | Manageability of hair under high humidity after successive three times application | 11 | 9 | 16 | 16 | 16 | 12 |

*: obtained by the reaction between behenic acid and dimethylaminopropylamine (fatty acid composition: $C_{18}/C_{20}/C_{22}/C_{24} = 1/9/88/2$)

Example 12

Pump Spray

|  | (% by mass) |
|---|---|
| Benzyl alcohol | 0.3 |
| 2-Benzyloxyethanol | 0.05 |
| Dipropylene glycol | 3.0 |
| Malic acid | 0.4 |
| Lactic acid | 0.4 |
| Glycerin | 1.0 |
| Ethanol | 5.0 |
| Perfume | 0.03 |
| Sodium hydroxide | adjusted to pH 3.7 (when diluted to 20 times its mass with water) |
| Water | Balance |

Example 13

Pump Mist

|  | (% by mass) |
|---|---|
| Benzyl alcohol | 0.5 |
| Dipropylene glycol | 4.0 |
| Malic acid | 0.6 |
| Lactic acid | 0.6 |
| Polyvinylpyrrolidone | 3.0 |
| Ethanol | 10.0 |
| Perfume | 0.02 |
| Sodium hydroxide | adjusted to pH 3.7 (when diluted to 20 times its mass with water) |
| Water | Balance |

Example 14

Hair Gel

|  | (% by mass) |
| --- | --- |
| Benzyl alcohol | 1.0 |
| Dipropylene glycol | 5.0 |
| Glycerin | 2.0 |
| Stearyl trimethylammonium chloride | 0.25 |
| Malic acid | 0.3 |
| Lactic acid | 0.3 |
| Hydroxyethyl cellulose | 2.0 |
| Ethanol | 5.0 |
| Perfume | 0.05 |
| Sodium hydroxide | adjusted to pH 3.7 (when diluted to 20 times its mass with water) |
| Water | Balance |

Example 15

Aerosol Spray

| <Stock Solution> | (% by mass) |
| --- | --- |
| Benzyl alcohol | 0.3 |
| Dipropylene glycol | 3.0 |
| Malic acid | 0.5 |
| Lactic acid | 0.5 |
| Stearyl trimethylammonium chloride | 0.25 |
| Glycerin | 1.0 |
| Perfume | 0.02 |
| Sodium hydroxide | adjusted to pH 3.7 (when diluted to 20 times its mass with water) |
| Water | Balance |

<Propellant>
Nitrogen Gas
<Stock Solution/Propellant Mass Ratio>99.5/0.5

Example 16

Pump Foam

|  | (% by mass) |
| --- | --- |
| Benzyl alcohol | 0.4 |
| Dipropylene glycol | 2.5 |
| Malic acid | 0.7 |
| Lactic acid | 0.7 |
| Polyoxyethylene (16) lauryl ether | 1.0 |
| Stearyltrimethylammonium chloride | 0.25 |
| Glycerin | 1.0 |
| Ethanol | 5.0 |
| Perfume | 0.03 |
| Sodium hydroxide | adjusted to pH 3.7 (when diluted to 20 times its mass with water) |
| Water | Balance |

Example 17

Aerosol Foam

| <Stock Solution> | (% by mass) |
| --- | --- |
| Benzyl alcohol | 1.0 |
| Dipropylene glycol | 7.0 |
| Malic acid | 1.0 |
| Lactic acid | 0.2 |
| Polyoxyethylene (16) lauryl ether | 1.0 |
| Cetyl trimethylammonium chloride | 0.25 |
| Glycerin | 1.0 |
| Ethanol | 4.5 |
| Perfume | 0.03 |
| Sodium hydroxide | adjusted to pH 3.7 (when diluted to 20 times its mass with water) |
| Water | Balance |

<Propellant>
LPG (0.44 MPa)
<Stock Solution/Propellant Mass Ratio>93.0/7.0

Example 18

Hair Lotion

|  | (% by mass) |
| --- | --- |
| Benzyl alcohol | 0.5 |
| Dipropylene glycol | 2.5 |
| Malic acid | 2.5 |
| Lactic acid | 2.5 |
| Stearyl trimethylammonium chloride | 0.12 |
| Cetyl trimethylammonium chloride | 0.12 |
| Polyethylene glycol 400 | 0.45 |
| Ethanol | 4.5 |
| Perfume | 0.03 |
| Sodium hydroxide | adjusted to pH 3.7 (when diluted to 20 times its mass with water) |
| Water | Balance |

What is claimed is:

1. A hair cosmetic composition, comprising the following Components (A) to (E):
   (A) benzyl alcohol, from 0.1 to 2% by mass;
   (B) dipropylene glycol, from 0.5 to 20% by mass;
   (C) malic acid or a salt thereof, from 0.2 to 10% by mass, in terms of the malic acid;
   (D) lactic acid or a salt thereof, from 0.2 to 10% by mass, in terms of the lactic acid; and
   (E) polyoxyethylene hydrogenated cator oil, 2% by mass or less,
   wherein a Component (E)/Component (A) mass ratio is from 0.5 to 5, and
   wherein a Component (B)/Component (A) mass ratio is from 1 to 50.

2. The hair cosmetic composition according to claim 1, wherein a total content of Components (C) and (D) is from 0.4 to 15% by mass.

3. The hair cosmetic composition according to claim 1, wherein a Component (B)/Component (A) mass ratio is from 3 to 45.

4. The hair cosmetic composition according to claim 1, further comprising 2-benzyloxyethanol as Component (F) at a concentration of 0.5% by mass or less and at a Component (F)/Component (A) mass ratio falling within a range of 0 to 0.5, wherein Component (F) is present in a non-zero amount.

5. The hair cosmetic composition according to claim 1, having a pH at 25° C. of from 3.0 to 5.0 when diluted to 20 times the mass with water.

6. A hair-quality improving method, comprising applying the hair cosmetic composition according to claim 1 to hair and leaving the hair without rinsing.

7. The hair-quality improving method according to claim 6, wherein the hair cosmetic composition is applied to the hair at least once in two days and, in total, at least two times.

8. The hair-quality improving method according to claim 6, wherein said leaving the hair without rinsing comprises leaving said cosmetic composition on the hair for at least 3 hours following said applying to the hair followed by rinsing said hair.

9. The hair-quality improving method according to claim 8, wherein said rinsing comprises shampooing.

10. The hair-quality improving method according to claim 6, wherein said leaving the hair without rinsing comprises leaving said cosmetic composition on the hair for at least 6 hours following said applying to the hair followed by rinsing said hair.

11. The hair-quality improving method according to claim 10, wherein said rinsing comprises shampooing.

\* \* \* \* \*